United States Patent [19]

Eriksoo et al.

[11] 4,172,074

[45] Oct. 23, 1979

[54] PREPARATION OF AN ANTIDEPRESSANT

[75] Inventors: Edgar Eriksoo; Sten S. Kelfve, both of Helsingborg, Sweden

[73] Assignee: Aktiebolaget Leo, Sweden

[21] Appl. No.: 697,764

[22] Filed: Jun. 21, 1976

[30] Foreign Application Priority Data

Jul. 3, 1975 [GB] United Kingdom ............... 28145/75

[51] Int. Cl.² .......................................... C07D 223/28
[52] U.S. Cl. ............................................... 260/239 D
[58] Field of Search ................................... 260/239 D

[56] References Cited
FOREIGN PATENT DOCUMENTS 1177525  1/1970  United Kingdom ............... 260/239 D

OTHER PUBLICATIONS

Eriksoo et al. (II), Arzheim.–Forsch (Drug Res.), 20, pp. 1561–1569 (1970).

*Primary Examiner*—Donald G. Daus
*Assistant Examiner*—D. B. Springer
*Attorney, Agent, or Firm*—Gordon W. Hueschen

[57] ABSTRACT

The present invention relates to a new and improved method for the preparation of the hydrochloride of 4'-chloro-2-{(3-(10,11-dihydro-5H-dibenz[b,f]azepinyl-(5))-propyl)-methyl-amino}-acetophenone, in the following called lofepramine hydrochloride. In the following, the free base is referred to as lofepramine.

6 Claims, No Drawings

PREPARATION OF AN ANTIDEPRESSANT

The present invention relates to a new and improved method for the preparation of the hydrochloride of 4'-chloro-2-{(3-(10,11-dihydro-5H-dibenz[b,f]azepinyl-(5)-propyl)-methyl-amino}-acetophenone, in the following called lofepramine hydrochloride. In the following, the free base is referred to as lofepramine.

BACKGROUND OF THE INVENTION

Lofepramine hydrochloride is a compound which has been found to be clinically effective against disorders related to the central nervous system, especially mental depressions. A method for the preparation of lofepramine hydrochloride is described in British patent Ser. No. 1,177,525, which also teaches broadly conditions under which the reaction may be carried out. A preferred version of this method is reported by E. Eriksoo and O. Rohte in Arzneimittelforschung 20, 1561–1569 (1970). However, this knowm method presents difficulties of a pronounced nature, especially when used in full-scale production. Thus, slight unintentional variations in the process conditions often result in discoloured products, which are very difficult to purify (see the comparative example hereinafter).

One of the underlying reasons for the problems which are encountered, when employing the known method and previously suggested conditions, is that the intermediate lofepramine cannot be isolated conveniently from the solvent in which it is formed, much less in solid form. Another reason is the fact that, in the known conventional method for preparation of amine hydrochlorides which involves addition of a solution of hydrogen chloride in an organic solvent to the base, it is very difficult if not impossible to provide the correct amount of hydrogen chloride. This is especially true when the exact content of the base is unknown. In the present situation the amount of hydrogen chloride is critical inasmuch as lofepramine hydrochloride is rapidly discoloured by excess of acid.

The present invention has for its purpose to provide an improved method by which the above-mentioned difficulties are avoided.

According to the invention, it has unexpectedly been found that by employing a two-phase system and by (I) contacting (a) 10,11-dihydro-5-(3-(methylamino)-propyl)-5H-dibenzo[b,f]azepine with (b) 2-bromo-4'-chloroacetophenone dissolved in a solvent (c) selected from the group consisting of alkanones, cycloalkanones, and alkyl alkanoates, which (1) are of molecular weights between about 60 and 150 and (2) in which the solubility of water is more than about 0.1% in the presence of (d) an aqueous phase which is buffered at a pH between about 6 and 9 with an inert buffer substance, the product (e) lofepramine is precipitated directly from the reaction mixture in pure, crystalline form and can be (II) isolated by conventional methods, such as filtration or centrifugation.

This observation, that the compound lofepramine could be spontaneously crystallized as a reaction product of these two starting materials, when employing the specific solvent which is utilized according to the present invention, provides the basis for advantageous results accomplished in the first step according to the present invention, and was indeed unpredictable. It was all the more unobvious in the light of previous experience with closely related compounds of the same general type and of the same general structure which, when prepared from analogous reactants and in the same solvent as employed according to the present invention, could not be crystallized as reaction products.

To effect step (III), conversion of lofepramine, obtained in the foregoing manner from step (II), into the hydrochloride, it is then (III a) dissolved in a liquid chlorohydrocarbon having not more than two carbon atoms wherein at least one carbon atom carries both hydrogen and chlorine-atoms, especially a solvent such as methylene chloride, chloroform, 1,1-dichloroethane, 1,2-dichloroethane, and trichloroethylene, and (III b) mixed together with an excess, preferably slightly more than the equivalent amount, of aqueous hydrochloric acid, usually by stirring, whereby the hydrochloride is formed in the organic phase or at the interface of the organic and the aqueous phases by reaction of stoichiometric proportions of the lofepramine and hydrogen chloride. The hydrochloride remains in the organic phase, from which it may be readily recovered.

The excess of the hydrochloric acid in the aqueous phase is preferably not more than about 50% over the stoichiometric quantity, if for no other reason than economy. The hydrochloride is then (III c) isolated from the organic solvent solution by evaporating to dryness, optionally in vacuum, and the residue may then be dissolved in an organic solvent, such as butanone, and readily crystallized therefrom.

This second step in the method of the invention, which involves a completely unconventional approach to the problem of forming the hydrochloric acid addition salt of the particular free basic tertiary amine intermediate by efficient contact between an aqueous phase containing a dissolved amount of hydrochloric acid in excess of the stoichiometric amount required for complete reaction with the intermediate, said intermediate being dissolved in a particular type of organic phase obviates the disadvantages experienced with previous practices for the preparation of the same end product from the same two reactants and allows procurement of the desired hydrochloric acid addition salt in unprecedented purity and without the undesirable discoloration which has characterized the product as produced by previously available procedure, despite the fact that considerable excess of the hydrochloric acid may be employed, which in turn makes exact measurement of the reactant quantities unnecessary.

The combination of these two steps into an integral process makes the attainment of these advantages, along with unprecedented yields and conversions, available with facility.

In the main reaction to form lofepramine, preferred solvents are such as ethyl acetate, methyl isobutylketone, octanone-2, heptanone-3, diisobutyl ketone, t-butylacetate, n-butylacetate, n-amylacetate, ethyl isobutyrate, butanone, cyclohexanone, propyl acetate, and isopropyl acetate. The especially preferred solvents are of molecular weight between about 60 and 105, and in which the solubility of water is more than about 0.5 percent. Ethyl acetate and methyl isobutyl ketone are particularly preferred.

The reaction is preferably carried out at a temperature within the range 10°–40° C., especially at room temperature, i.e., 20°–25° C. Suitable buffer substances are alkali hydrogen carbonates, carbonates and phosphates.

The lofepramine hydrochloride obtained by the method of this invention, as previously noted, has considerably improved purity and appearance and the process has been found to be well suited for production on a large scale. The product can be used for the intended purpose without further purification.

The invention will now be described by non-limiting examples.

EXAMPLE 1

Fifty kgs of 10,11-dihydro-5-(3-(methylamino)-propyl)-5H-dibenz[b,f]azepine hydrochloride are dissolved in 150 l of water and fifty l of ethyl acetate are added followed by 16.8 l of a ten Molar sodium hydroxide aqueous solution. The temperature is adjusted to 20°–24° C. 22.2 kgs of sodium hydrogen carbonate are added followed by 42.4 kgs of 2-bromo-4'-chloroacetophenone in four equal portions every fifteen minutes while stirring the reaction mixture efficiently. The stirring is continued for two hours, during which time a white precipitate appears. Thereafter, the precipitate of lofepramine is filtered off and washed with fifty l of water, fifty l of methanol, and finally with fifty l of water. The intermediate product so obtained is dissolved in 100 l of methylene chloride and stirred for one hour with a solution of thirteen l of concentrated hydrochloric acid in fifty l of water. The methylene chloride solution is separated, dried over anhydrous sodium sulphate, and thereafter evaporated in vacuo to dryness.

The oily residue is crystallized from 175 l of butanone and 66 kgs of lofepramine hydrochloride are obtained, m.p. 152°–4° C., corresponding to an overall yield of about 88%.

EXAMPLE 2

The procedure of Example 1 is repeated, substituting any of methyl isobutyl ketone, cyclohexanone, butanone, propyl acetate, and isopropyl acetate, for the ethyl acetate used in Example 1. Similar results are obtained.

EXAMPLE 3

The procedure of Example 1 is repeated, substituting any of chloroform, 1,1-dichloroethane, trichloroethylene, and 1,2-dichloroethane for the methylene chloride used in Example 1. Similar results are obtained.

COMPARATIVE EXAMPLE 10,11-Dihydro-5-(3-(methylamino)propyl)-5H-dibenz[b,f]azepine hydrochloride (5.7 kg) are dissolved in 15 l of water and 35 l of benzene are added followed by 4.24 kg of 2-bromo-4'-chloroacetophenone in four equal portions every 15 minutes while stirring the reaction mixture efficiently. The stirring is continued at room temperature for two hours. The aqueous phase is separated and discarded. The organic phase is washed with 1 l of 2 M aqueous hydrochloric acid and water and 6.2 l of 3 M solution of hydrogen chloride in ethyl ether are added. The resulting mixture is evaporated to dryness in vacuo and the residue is dissolved in 25 l of butanone. After cooling lofepramine hydrochloride crystallizes in form of greenish-grey crystals and is filtered off yield: 5.2 kg, m.p. 150°–2°. Recrystallization from butanone does not remove the discoloration. Unfavourable results are also obtained when the reaction is carried out in toluene, methylene chloride, chloroform, acetone, methylacetamide, methanol, and ethanol.

It is to be understood that the invention is not limited to the exact details of operation or exact compounds shown and described, as obvious modifications and equivalents will be apparent to one skilled in the art, and the invention is therefore to be limited only by the scope of the appended claims.

We claim:

1. In a process for the preparation of crystalline lofepramine free base from 10,11-dihydro-5-(3-(methylamino)-propyl)-5H-dibenz[b,f]azepine, the improvement which comprises using a two-phase system and employing the steps of
   (I) contacting (a) 10,11-dihydro-5-(3-(methylamino)-propyl)-5H-dibenz[b,f]azepine with (b) 2-bromo-4'-chloroacetophenone in (c) a solvent selected from the group consisting of unsubstituted alkanones, cycloalkanones, and alkyl alkanoates (1) having molecular weights between 60 and 150 and (2) in which the solubility of water is more than about 0.1%, in the presence of (d) an aqueous phase having a buffered pH between about 6 and 9, to form (e) a precipitate of lofepramine free base, and
   (II) isolating said precipitated lofepramine free base.

2. In a process for the preparation of the crystalline hydrochloride of lofepramine, the improvement which comprises carrying out the process of claim 1 and the further steps of
   (III a) dissolving the isolated lofepramine from step (II) in a liquid chlorohydrocarbon having not more than two carbon atoms wherein at least one carbon atom carries both hydrogen and chlorine-atoms,
   (III b) mixing the thus-obtained solution with aqueous hydrochloric acid in an amount at least equivalent to the amount of dissolved lofepramine, and
   (III c) recovering the resulting lofepramine hydrochloride from the organic phase by evaporation.

3. Process of claim 1, wherein the solvent is one which has a molecular weight between 60 and 105 and in which the solubility of water is more than about 0.5%.

4. Process of claim 1, wherein the solvent is selected from the group consisting of ethyl acetate, methyl isobutyl ketone, butanone, cyclohexanone, propyl acetate, octanone-2, heptanone-3, diisobutyl ketone, t-butylacetate, n-butylacetate, n-amylacetate, ethyl isobutyrate and isopropyl acetate.

5. Process of claim 3, wherein the solvent is selected from the group consisting of ethyl acetate and methyl isobutyl ketone.

6. Process of claim 2, wherein the halogenated hydrocarbon solvent is selected from the group consisting of methylene chloride, chloroform, 1,1-dichloroethane, 1,2-dichloroethane, and trichloroethylene.

* * * * *

UNITED STATES PATENT AND TRADEMARK OFFICE
CERTIFICATE OF CORRECTION

PATENT NO. : 4,172,074
DATED : October 23, 1979
INVENTOR(S) : Eriksoo et al.

It is certified that error appears in the above—identified patent and that said Letters Patent is hereby corrected as shown below:

[56] OTHER PUBLICATIONS; "Arzheim" should read -- Arzneim --

Col. 1, line 7; "(5)-" should read -- (5))- --
Col. 1, line 21; "knowm" should read -- known --
Col. 1, line 48; "dibenzo[" should read -- dibenz[ --
Col. 1, line 64; "for advantageous" should read -- for the advantageous --
Col. 2, lines 37 & 38; "phase obviates" should read -- phase, obviates --

Signed and Sealed this

Fifteenth Day of January 1980

[SEAL]

Attest:

SIDNEY A. DIAMOND

Attesting Officer

Commissioner of Patents and Trademarks